(12) United States Patent  
Clegg et al.

(10) Patent No.: US 7,837,034 B2
(45) Date of Patent: *Nov. 23, 2010

(54) TEMPORARY MEDICAL INSTRUMENT HOLDER BOX WITH LATERAL INSTRUMENT HOLDER APERTURE

(75) Inventors: Trent Clegg, Lehi, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 450 days.

This patent is subject to a terminal disclaimer.

(21) Appl. No.: 11/538,761

(22) Filed: Oct. 4, 2006

(65) Prior Publication Data

US 2007/0119738 A1   May 31, 2007

Related U.S. Application Data

(63) Continuation-in-part of application No. 11/290,935, filed on Nov. 30, 2005.

(51) Int. Cl.
  *B65D 85/24* (2006.01)
(52) U.S. Cl. .................. 206/366; 206/365; 206/370
(58) Field of Classification Search .............. 206/365, 206/366, 369, 370, 382, 571
  See application file for complete search history.

(56) References Cited

U.S. PATENT DOCUMENTS

| | | | |
|---|---|---|---|
| 0,964,406 A | 7/1910 | DeWitt | |
| 4,243,140 A * | 1/1981 | Thrun | 206/380 |
| 4,380,292 A | 4/1983 | Cramer | |
| 4,919,264 A | 4/1990 | Shinall | |
| 4,936,449 A | 6/1990 | Conard et al. | |
| 5,265,724 A | 11/1993 | Dondlinger | |
| 5,311,985 A | 5/1994 | Suida | |
| 5,417,505 A | 5/1995 | Voorhees | |
| 5,462,163 A | 10/1995 | Berry | |
| 5,538,132 A | 7/1996 | Propp et al. | |
| 5,626,230 A * | 5/1997 | Shanley et al. | 206/571 |
| 5,850,917 A | 12/1998 | Denton et al. | |
| 5,967,778 A | 10/1999 | Riitano | |

(Continued)

OTHER PUBLICATIONS

Office Action dated Jan. 12, 2010 for U.S. Appl. No. 11/538,767.

(Continued)

*Primary Examiner*—Mickey Yu
*Assistant Examiner*—Sharon M Prange
(74) *Attorney, Agent, or Firm*—Stoel Rives LLP

(57) ABSTRACT

A temporary instrument holder having one or more lateral surface instrument holder apertures configured to receive needles therein. The lateral surface instrument holder aperture is provided in addition to a top surface instrument holder portion and is positioned in the side of the temporary instrument holder allowing sharp implements to be inserted into the lateral surface instrument holder aperture to minimize tipping of the temporary instrument holder. A portion of the implement positioned in the lateral instrument holder aperture can rest on the support surface on which the temporary instrument holder is positioned. A boundary septum is provided between the lateral surface instrument holder aperture and the instrument holder portion on the top surface to prevent passage of the needle apparatus from the need stop portion to the lateral surface instrument holder aperture to prevent an inadvertent stick or puncture the skin of a practitioner.

18 Claims, 9 Drawing Sheets

U.S. PATENT DOCUMENTS

| | | | |
|---|---|---|---|
| 5,975,295 A | 11/1999 | Diamond | |
| 6,279,743 B1 | 8/2001 | Ballard et al. | |
| 6,530,479 B2 * | 3/2003 | Hernandez | 206/572 |
| 6,827,212 B2 * | 12/2004 | Reaux | 206/372 |
| 7,070,051 B2 * | 7/2006 | Kanner et al. | 206/382 |
| 7,159,714 B2 | 1/2007 | Wilkinson et al. | |
| 2003/0024891 A1 | 2/2003 | Diamond | |
| 2007/0119739 A1 | 5/2007 | Clegg et al. | |
| 2007/0119740 A1 | 5/2007 | Clegg et al. | |

OTHER PUBLICATIONS

Office Action dated May 29, 2009 for U.S. Appl. No. 11/538,767.
Office Action dated Sep. 5, 2008 for U.S. Appl. No. 11/538,767.
Office Action dated Dec. 28, 2009 for U.S. Appl. No. 11/290,935.
Office Action dated Mar. 31, 2009 for U.S. Appl. No. 11/290,935.
Office Action dated Jul. 9, 2008 for U.S. Appl. No. 11/290,935.
Office Action dated Jul. 20, 2010 for U.S. Appl. No. 11/538,767.
Office Action dated Aug. 3, 2010 for U.S. Appl. No. 11/290,935.

* cited by examiner

TEMPORARY MEDICAL INSTRUMENT HOLDER BOX WITH LATERAL INSTRUMENT HOLDER APERTURE

CROSS-REFERENCE TO RELATED APPLICATIONS

This application is a continuation-in-part of U.S. patent application Ser. No. 11/290,935, filed Nov. 30, 2005, which is incorporated herein by reference in its entirety. This application also incorporates by reference in its entirety U.S. patent application Ser. No. 11/538,767, filed Oct. 4, 2006.

BACKGROUND

The present invention relates to a temporary instrument holder. In more particular, the present invention relates to a temporary holder for medical instruments, such as needles, trocars, scalpels or other devices or implements. The temporary holder includes a lateral instrument holder aperture.

In recent years, increased attention has been directed by medical practitioners and the medical community as a whole to blood borne illnesses and infections. The potential for the transmission of blood borne illnesses from patients to practitioners has heightened the awareness of safety standards to protect against inadvertent practitioner infection. A variety of new safety practices and regulations have been developed dictating procedures to be followed before, during, and after surgery as well as during the routine care of patients. For example, special procedures and cautions are recommended and/or required for interactions with patients involving bodily fluids, the handling of medical apparatus that have been utilized in connection with the bodily fluids of patients, and for the disposal of bodily fluids and other biological materials.

As a part of the new safety emphasis with regard to blood borne illnesses and infections, particular attention has been directed to the handling of needles, trocars, or other "sharps." Such sharps have been a subject of increased focus due to the potential for accidental puncture of the practitioner's skin and consequent transmission of disease to the practitioner. A number of devices have been developed to protect against accidental punctures while utilizing sharps. For example, self-deploying needle shields, which can be readily actuated with limited risk of inadvertent puncturing of a practitioner, have been provided on a number of needles and other trocar type apparatus. Specialized depositories for the receipt and containment of used needles have also been developed which provide for safe and simple disposition of sharps.

Another type of device which has been developed to prevent needle sticks or other punctures of a practitioner are temporary needle holders. Such temporary needle holders are adapted to be utilized in a surgical field for holding a needle or other sharp implement that has been utilized or is intermittently utilized during the course of the procedure. Such temporary needle holders typically have a needle holder field in which the needles can be inserted while they are not being used. The temporary needle holder provides a location for the holding of needles that are not being utilized, such that the needles are not left on the surgical surface in a manner that they may inadvertently stick or puncture the skin of a practitioner during the course of the procedure.

Typically, such temporary needle holders are configured to be fairly small. Smaller temporary needle holders are typically desired due to surgical surface ergonomics and the fact that a limited number of needles are typically utilized in a procedure. For example, typically the number and types of surgical tools, implements, and containers placed in the surgical field for use during the procedure are sufficient that a limited amount of space is available for each apparatus. Due to the limited number of needles that are utilized in typical procedures, a fairly small temporary needle holder is sufficient to hold the number of needles needed during the procedure. Because a fairly small number of needles are typically utilized and the size requirements for additional needles are quite minimal, a larger unit is typically inefficient due to unused space on the needle holder field. Elimination of unused space on the needle holder field typically creates greater efficiencies in usage of materials, storage/shipping size, and per unit weight.

One problem associated with such smaller and/or lighter devices, is that where a practitioner is utilizing a larger needle and syringe combination or a partially-filled syringe, placement of the needle and syringe in the temporary needle holder can result in disadvantageous tipping of the temporary needle holder. Not only can such tipping be unpredictable, but the tipping can make it difficult to utilize the temporary needle holder and the needles and/or syringes positioned therein during the course of the procedure. Additionally, tipping of a partially-filled syringe can result in turbulence in the contents of the syringe that may introduce air bubbles into the syringe. As a result, valuable surgical time may be consumed de-bubbling the syringe in preparation for injection of the contents of the syringe into the patient.

BRIEF SUMMARY OF EMBODIMENTS OF THE INVENTION

Embodiments of the present invention are directed to a temporary instrument holder for medical instruments, including sharps such as needles, trocars, scalpels or other devices or implements, having a lateral surface instrument holder aperture configured to receive instruments therein. Typically, the lateral surface instrument holder aperture is positioned in a side surface of the temporary instrument holder allowing needles, trocars, or other sharp implements to be inserted into the lateral surface instrument holder aperture in a manner which minimizes tipping of the temporary instrument holder.

Throughout the specification, "sharps" is used to describe any instrument or device that poses a contamination risk to people, such as medical personnel, by disruption of the skin. Examples of sharps may include, but are not limited to, sharp instruments such as needles, trocars, scalpels, and other dangerous implements with edges or surfaces that can cut or puncture.

In one embodiment, the lateral surface instrument holder aperture is provided in addition to a top surface instrument holder field. Thus, needle tips, scalpels, or other needle and sharps apparatus, can be inserted into the instrument holder field simultaneously. Larger medical instruments such as larger needles, partially-filled needles, scalpels or other sharps can be positioned in the lateral surface instrument holder aperture. A portion of the instrument can rest on the support surface on which the temporary instrument holder is positioned. Resting a portion of the instrument on the support surface minimizes tipping of the temporary instrument holder. When an instrument is positioned in the lateral surface instrument holder aperture, the instrument is positioned out of the way of movement of the practitioner that may knock, result in breakage, or otherwise disrupt the instrument. Additionally, the unique position of lateral surface instrument holder aperture allows a practitioner to easily and quickly identify and acquire an instrument positioned in the lateral surface instrument holder aperture.

According to one embodiment of the present invention, a boundary septum is provided between the lateral surface instrument holder aperture and the instrument holder field on the top surface. The boundary septum may be a protective structure which prevents migration of a needle tip or other implement from the instrument holder field to the lateral surface instrument holder aperture, or vice versa. By preventing migration of a needle tip, potential breakage of a secondary needle apparatus by the migrating needle can be prevented.

Preventing migration of needle tips may also minimize the potential that a needle tip could inadvertently stick or puncture the skin of a practitioner. For example, a needle tip could migrate from one instrument holder field, pass through a secondary instrument holder field, exit from a secondary instrument holder aperture, and puncture the skin of the practitioner holding the temporary instrument holder. In another embodiment, a plurality of lateral surface instrument holder apertures are provided. The use of a plurality of lateral surface instrument holder apertures allow the placement of two or more needles into lateral surface instrument holder apertures.

According to one embodiment of the invention, the temporary instrument holder includes a lid to enclose an instrument holder field. When the lid is closed, the lid may effectively serve as a boundary septum for the lateral surface instrument holder. Serving as a boundary septum, the lid helps to reduce the risk of skin puncture when a practitioner inserts a medical implement, such as a scalpel, into the lateral surface instrument holder aperture.

The foregoing and other aspects of the present invention will become more fully apparent from the following description and appended claims.

BRIEF DESCRIPTION OF THE DRAWINGS

In order to describe the manner in which the above-recited and other aspects of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF EXAMPLE EMBODIMENT OF THE INVENTION

The present invention is directed to a temporary instrument holder having a lateral surface instrument holder aperture configured to receive medical instruments, including sharps such as needles, scalpels trocars, therein. Typically, the lateral surface instrument holder aperture is positioned in a side surface of the temporary instrument holder allowing needles, trocars, or other sharp implements to be inserted into the lateral surface instrument holder aperture in a manner which minimizes tipping of the temporary instrument holder.

In one embodiment, the lateral surface instrument holder aperture is provided in addition to an instrument holder field in a top surface of the instrument holder aperture. Thus, smaller instruments, such as needles, can be inserted into the top surface instrument holder field. Larger medical instruments such as larger needles, partially-filled syringes, scalpels or other sharps can be positioned in the lateral surface instrument holder aperture. A portion of the instrument can rest on the support surface on which the temporary instrument holder is positioned. Resting of the instrument on the support surface minimizes tipping of the temporary instrument holder. When an instrument is positioned in the lateral surface instrument holder aperture, the instrument is positioned out of the way of movement of the practitioner, limiting disruption, damage, or breakage that may occur from the practitioner inadvertently contacting the instrument and/or instrument holder. Additionally, the unique position of the lateral surface instrument holder aperture allows a practitioner to easily and quickly identify and acquire an instrument positioned in the lateral surface instrument holder aperture.

Figure 1:
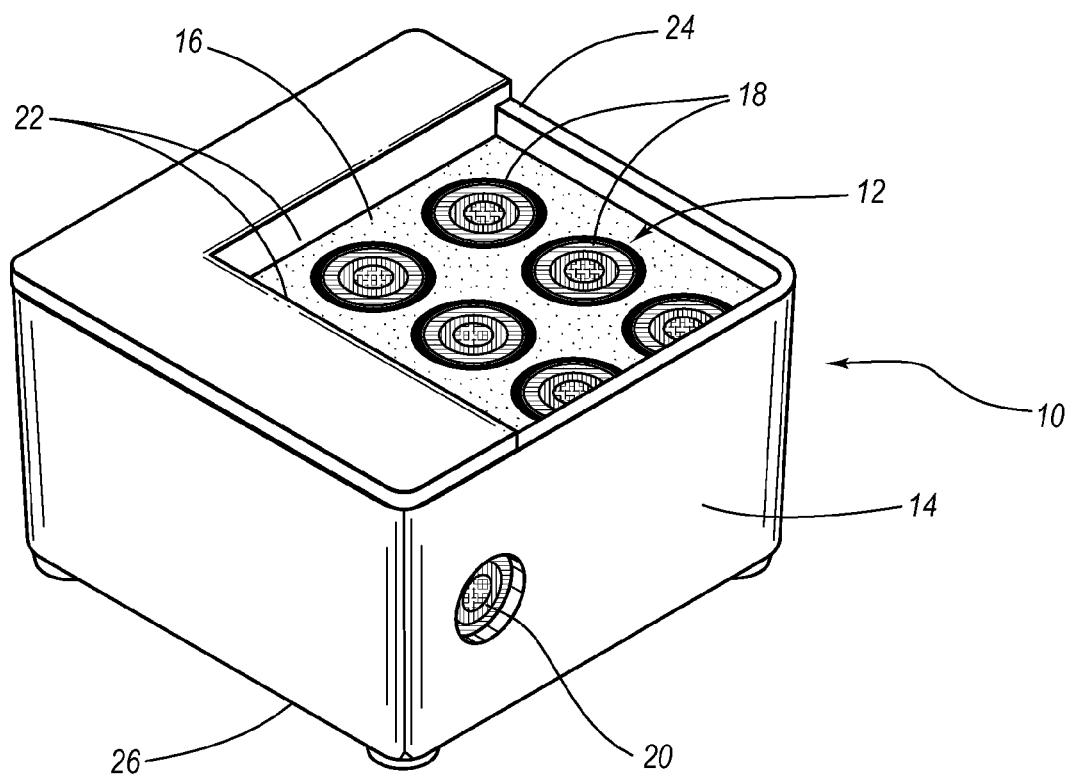
FIG. 1 is a perspective view of a temporary instrument holder illustrating a lateral surface instrument holder aperture.

FIG. 1 is a perspective view of temporary instrument holder 10, according to one embodiment of the present invention. In the illustrated embodiment, temporary instrument holder 10 has a lateral surface instrument holder aperture 20, which is utilized to allow for insertion of instruments into the side of the temporary instrument holder 10. Among other things, this arrangement may help to minimize tipping of temporary instrument holder 10. In the illustrated embodiment, temporary instrument holder 10 includes a top surface 12, a side surface 14, an instrument holder field 16, a lateral surface instrument holder aperture 20, a boundary septum 22, a rim 24, and a bottom 26.

Top surface of temporary instrument holder 12 includes instrument holder field 16. Top surface 12 of temporary instrument holder 10 is configured such that it is facing upward allowing it to be easily viewed and accessed by the practitioner. Targets 18 are positioned in the instrument holder field to provide a visual identification of potential placement areas for needles, trocars, or other sharp implements or tools that have been utilized during the course of the procedure. A practitioner can insert smaller and/or lighter needle apparatus, such as needle tips, emptied syringes, or an IV trocar into top surface 12.

During the course of the procedure, it is not uncommon that larger medical instruments, such as larger needles, trocars, scalpels, may be utilized. Additionally, it is not uncommon that a partially-filled syringe might need to be inserted into the temporary instrument holder 10 during the course of the procedure. Lateral surface instrument holder aperture 20 is positioned in the side surface 14 of the temporary instrument holder 10 in a manner that the practitioner can insert larger and/or heavier instruments into the lateral surface needle surface aperture 20. Lateral surface instrument holder aperture 20 provides not only a supplementary instrument holder field for insertion of sharps instruments, but is also positioned relatively close to the surgical surface, allowing the instrument to rest on the surgical surface and minimizing tipping of the temporary instrument holder. The lateral surface instrument holder aperture provides a location for inserting a needle or other sharp device into a second side of the temporary instrument holder.

Boundary septum 22 is positioned adjacent a lateral side of instrument holder field 16. In one embodiment, boundary septum 22 comprises a hardened layer or other puncture impervious or puncture resistant layer, such as plastic, metal, or other suitable material, configured to prevent the passage of the tips of needles, trocars, or other sharp implements from the instrument holder field to the lateral surface instrument holder aperture. Boundary septum 22 minimizes migration of needle tips into adjacent instrument holder fields that may cause damage to the medical instruments. Boundary septum 22 also limits the passage of needle tips from instrument holder field 16 to lateral surface instrument holder aperture 20, and from lateral surface instrument holder aperture 20 to instrument holder field 16. In this way, boundary septum 22 may prevent injury to the practitioner through inadvertent contact with a sharp instrument.

Rim 24 is positioned to provide an outer boundary for instrument holder field 16. Rim 24 creates a slight recess between top surface 12 of a temporary instrument holder 10 and the elevation of instrument holder field 16. In this manner, rim 24 prevents inadvertent slipping of needles, sharps, or other implement from the top surface of the instrument holder field 16 to the exterior of the temporary instrument holder 10. In this manner, a practitioner can safely grasp the temporary instrument holder 10 and insert a needle into the instrument holder field 16. In the event that the needle slips or does not entirely puncture the instrument holder field 16, the tip of the needle will typically be caught by rim 24, preventing additional slipping and puncturing of the practitioner in an unexpected manner.

Bottom 26 is positioned on the side of temporary instrument holder opposite top surface 12. Bottom 26 is configured to be positioned on a surgical or other medical work surface on which the temporary instrument holder is to be utilized. In one embodiment, bottom 26 includes a non-slip surface or adhesive surface which facilitates retention of the temporary instrument holder 10 on the surgical surface and additionally prevents tipping of the temporary instrument holder 10.

As will be appreciated by those skilled in the art, a variety of types and configurations of temporary instrument holder can be provided without departing from the scope and spirit of the present invention. For example, in one embodiment, a different number and configuration of targets are provided in the instrument holder field. In another embodiment, the lateral surface instrument holder aperture is of a different size, shape and/or configuration. In another embodiment, the temporary instrument holder may not include a boundary septum.

Figure 2:
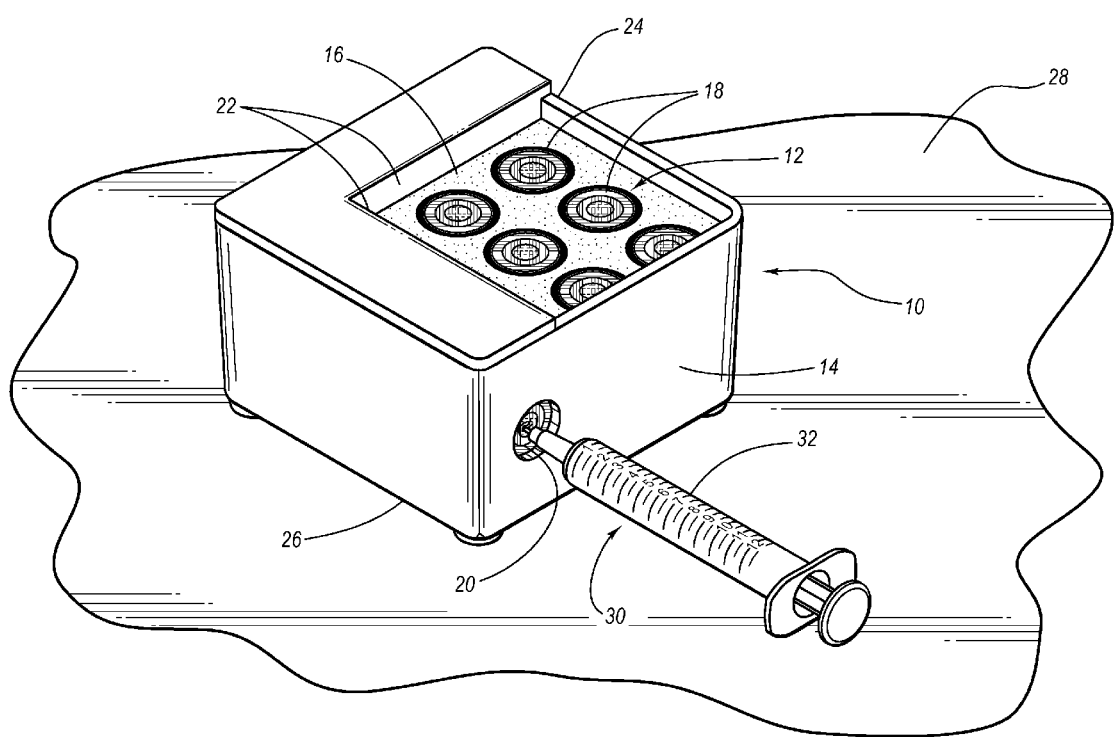
FIG. 2 is a perspective view of a temporary instrument holder of FIG. 1, illustrating a needle inserted into the lateral surface instrument holder aperture.

FIG. 2 is a perspective view of the temporary instrument holder 10 of FIG. 1, illustrating a needle syringe combination 30 inserted into lateral surface instrument holder aperture 20. In the illustrated embodiment, a syringe portion of needle syringe combination 30 is partially filled with a fluid 32. Fluid 32, positioned in the syringe portion of needle syringe combination 30, substantially adds to the weight of needle syringe combination 30. Additionally, the length of the needle portion of the needle syringe combination 30 creates a higher center of gravity, which can add to the likelihood of tipping of temporary instrument holder 10 should needle syringe combination 30 be positioned or inserted in instrument holder field 16. Additionally, a practitioner may simply desire to position needle syringe combination 30 in a separate location away from other needles or sharp implements. By providing a separate location for the insertion of needles and other sharps implements, instrument holder field 16 can also help to more readily identify needle syringe combination 30 as an implement which the practitioner may desire to utilize later in the procedure being performed.

In the illustrated embodiment, needle syringe combination 30 is inserted in lateral surface instrument holder aperture 20. Needle syringe combination 30 is shown positioned at a slight angle, such that the rearward portion of needle syringe combination 30 is in contact with support surface 28. By being in contact with support surface 28, needle syringe combination 30 is sufficiently supported to prevent breakage, or other damage, of needle syringe combination 30. Additionally, needle syringe combination 30 is supported in a manner that minimizes tipping of temporary instrument holder 10. In this manner, desired and intended positioning of temporary instrument holder 10 is maintained, allowing a practitioner to quickly identify instrument holder field 16 for the insertion of additional needles, sharps, or other tools or implements, while also being able to quickly identify the positioning of lateral surface instrument holder aperture 20 and needle syringe combination 30 positioned therein.

Figure 3:
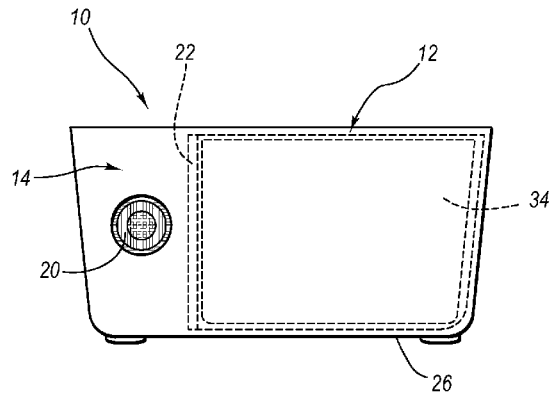
FIG. 3 is a side view of a temporary instrument holder illustrating a top instrument holder cushion layer, relative to a lateral surface instrument holder aperture.

FIG. 3 is a side view of temporary instrument holder 10, illustrating a top instrument holder cushion layer 34 in phantom lines. The positioning of top instrument holder cushion layer 34 relative to lateral surface instrument holder aperture 20 is also shown. As previously discussed, lateral surface instrument holder aperture 20 is positioned in side surface 14 of temporary instrument holder 10. Top instrument holder cushion layer 34 represents the total volume of the cushion layer associated with a instrument holder field that is available to receive needles, trocars, or other sharp implements from the instrument holder field.

In the illustrated embodiment, top instrument holder cushion layer 34 extends below the location of lateral surface needle aperture 20. Boundary septum 22 runs from top surface 12 of temporary instrument holder 10 to the bottom 26 of temporary instrument holder 10. In this manner, boundary septum 22 provides a complete and effective boundary to control the passage of needles, sharps, or other implements from instrument holder cushion layer 34 to lateral surface instrument holder aperture 20.

In the illustrated embodiment, the material from which top instrument holder cushion layer 34 is formed, comprises a non-coring resilient foam material. The non-coring quality of cushion layer 34 allows a needle to be inserted into top instrument holder cushion layer 34 and withdrawn without leaving a noticeable hole. In this manner, a secondary implement can be reinserted into the same position without weakening or minimizing the ability of cushion layer 34 to retain the secondary implement, subsequent to the earlier insertion. Other materials of comparable functionality and characteristics may be employed.

As will be appreciated by those skilled in the art, a variety of types and configurations of temporary instrument holder can be utilized without departing from the scope and spirit of the present invention. For example, in one embodiment the boundary septum extends only a portion of the length from the top surface of the instrument holder cushion layer to the bottom of the instrument holder cushion layer. In another embodiment a variety of types and configuration of cushion materials are be utilized. For example, in one embodiment, a thermalplastic rubber layer can be utilized. In another embodiment, another resilient polymer-based material can be utilized. In another embodiment, small layers of foam can be positioned adjacent one another in a manner to retain a needle or other sharp implement.

Figure 4:
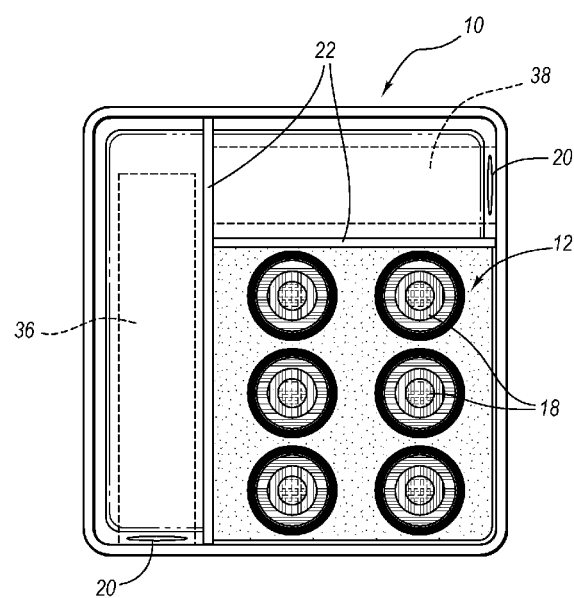
FIG. 4 is a top view of a temporary instrument holder illustrating a plurality of lateral surface instrument holder cushion layers associated with a plurality of lateral surface instrument holder apertures.

FIG. 4 is a top view of the temporary instrument holder 10 illustrating the juxtaposition of the side instrument holder cushion layers 36, 38 relative to the instrument holder field. In the illustrated embodiment, side instrument holder cushion layers 36, 38 are positioned on two sides of instrument holder field 16. Side instrument holder cushion layers 36, 38 extend along the length of the outer boundary of the instrument holder field 16. As explained with reference to FIG. 3, boundary septum 22 provides an effective barrier between top instrument holder cushion layer 34 and side instrument holder cushion layers 36, 38. By providing first and second side instrument holder cushion layers 36, 38, a practitioner can insert more than one implement into a lateral surface instrument holder aperture. This allows the placement of multiple syringes in the event that multiple syringes may need to be utilized during the course of the procedure or in the event that multiple heavy needle/syringe combinations or other implements are utilized.

Figure 5A:
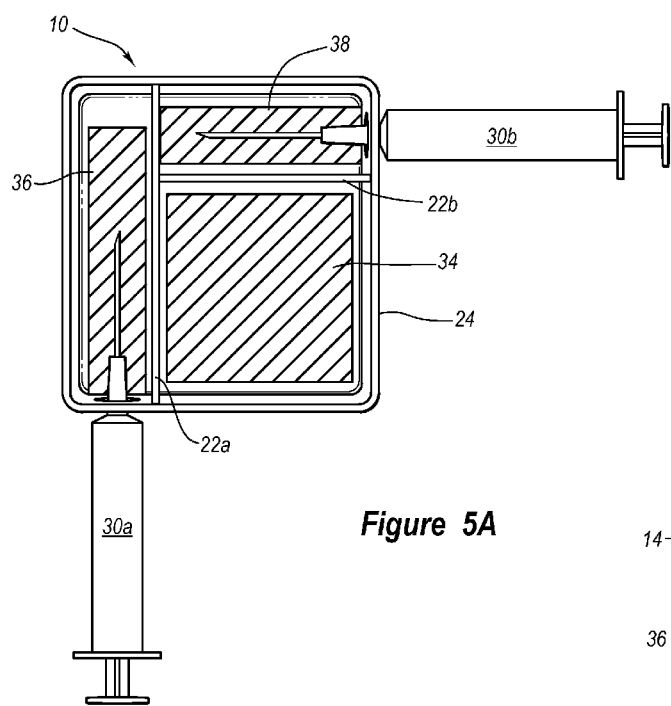
FIG. 5A is a top cross-sectional view illustrating a plurality of needle syringe combination units inserted into side instrument holder cushion layers.

FIG. 5A is a top cross-sectional view of a temporary instrument holder 10 according to one embodiment of the present invention. In the illustrated embodiment, the tips of needle syringe combinations 30a and 30b are inserted into side instrument holder cushion layers 36 and 38. In the illustrated embodiment, it can be seen that the length of the needle syringe combinations 30a and 30b are sufficiently long that, in the absence of boundary septums 22a, 22b, the needles could extend from the side instrument holder cushion layers 36, 38 and into the top instrument holder cushion layer 34 and out of the associated instrument holder field 16 (see also FIG. 5B).

Use of side instrument holder cushion layers 36, 38 provides two additional points of placement for needles, trocars, or other sharp implements, in addition to the instrument holder field 16 (see FIG. 1). Side instrument holder cushion layers 36, 38 and their associated lateral instrument holder apertures allow the practitioner to more easily keep track of particular needles, syringes, and associated medicinal fluids contained therein to be utilized in subsequent portions of the procedure. Additionally, the needles 30a and 30b can rest on the support surface on which the temporary instrument holder 10 is positioned. This minimizes potential breaking of the tips of the needles 30a, 30b while also minimizing tipping of the temporary instrument holder 10. In the illustrated embodiment, boundary septum 22a extends along the entire length of temporary instrument holder 10, such that the tip of needle syringe combination 30b is prevented from contacting the tip of needle syringe combination 30a in a manner that may cause damage, the exchange of fluids, or other contamination of needle syringe combination 30a from needle syringe combination 30b.

Figure 5B:
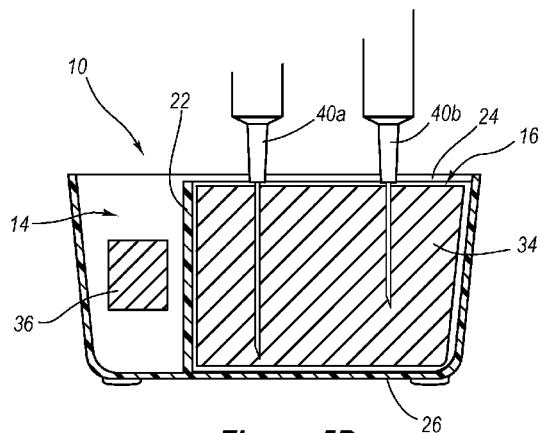
FIG. 5B is a cross-sectional view of a temporary instrument holder, illustrating a plurality of needle tips inserted into a top instrument holder cushion layer.

FIG. 5B is a cross-sectional side view of a temporary instrument holder 10 in which needle tips 40a, b have been inserted into a top instrument holder cushion layer 34. In the illustrated embodiment, it can be seen that rim 24 of temporary instrument holder 10 extends above the top surface of the instrument holder field 16. Needle tips 40a, b have been inserted into top instrument holder cushion layer 34, such that the distal ends of the needle tips 40a, b extend a given amount into the top instrument holder cushion layer. The length of needle tip 40a is substantially longer than that of needle tip 40b. It can be appreciated that, in the absence of a boundary septum 22 and in the event that needle tip 40a is inserted at an angle into top instrument holder cushion layer 34, the point of needle tip 40a could extend out through the side instrument holder cushion layer 36 and associated lateral surface instrument holder aperture 20 (see FIG. 1) in a manner that could result in inadvertent sticking or puncture of the practitioner who may be holding the temporary instrument holder 10.

As will be appreciated by those skilled in the art, a variety of types and configurations of the temporary instrument holder can be provided without departing from the scope and spirit of the present invention. For example, in one embodiment, the shape of the temporary instrument holder is rectangular. In another embodiment, the shape of the temporary instrument holder is other than a square or rectangle. In another embodiment, the sides of the instrument holder cushion layers completely fill the inside of the temporary instrument holder, such that the instrument holder cushion layers are only bounded by the outside edges of the temporary instrument holder and the boundary septa.

Figure 6A:
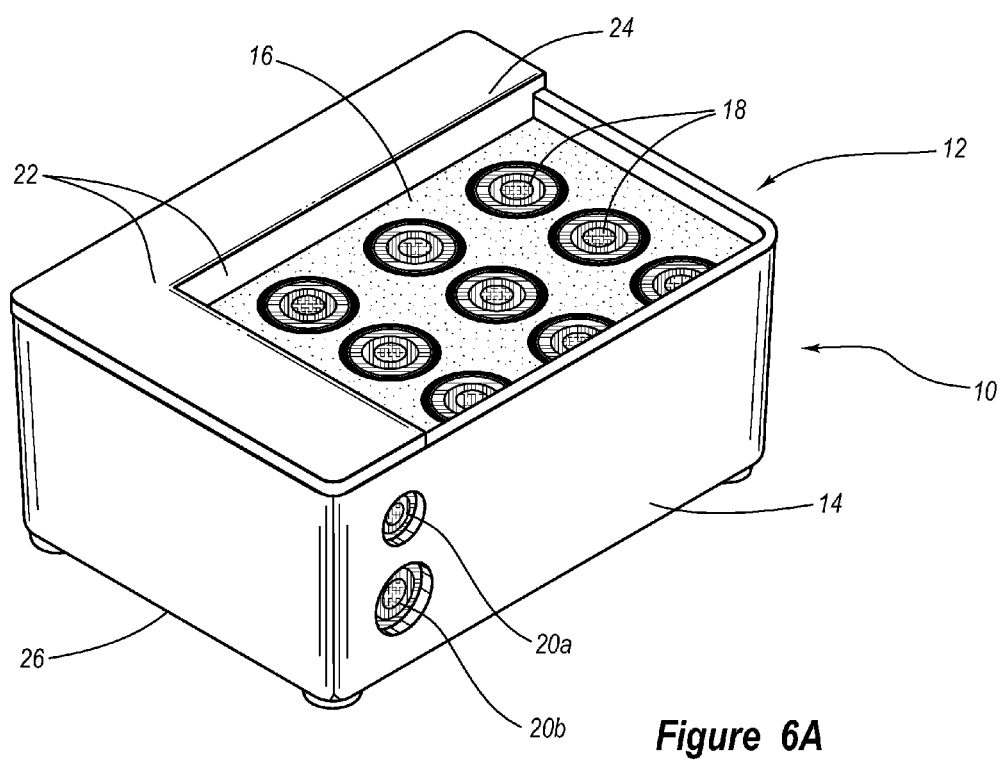
FIGS. 6A and 6B are perspective views of a temporary instrument holder, according to alternative embodiments of the present invention.

FIG. 6A is a perspective view of an alternative embodiment of the present invention. In the illustrated embodiment, a first lateral surface instrument holder aperture 20a and a second lateral surface instrument holder aperture 20b are positioned in the side surface 14 of the temporary instrument holder 10. In the illustrated embodiment, first lateral surface instrument holder aperture 20a is positioned above second lateral surface instrument holder aperture 20b. Second lateral surface instrument holder aperture 20b is larger than first lateral surface instrument holder aperture 20a. This allows larger needle syringe combinations to be placed in second lateral surface instrument holder aperture 20b. As a result, a smaller needle syringe combination inserted into first lateral surface instrument holder aperture 20a can rest directly on a larger needle syringe combination placed in second lateral surface instrument holder aperture 20b. A plurality of lateral surface instrument holder apertures can be provided in the same side surface of temporary instrument holder 10, providing additional placement locations and potential sharps device organization by the practitioner during the course of the procedure.

Figure 6B:
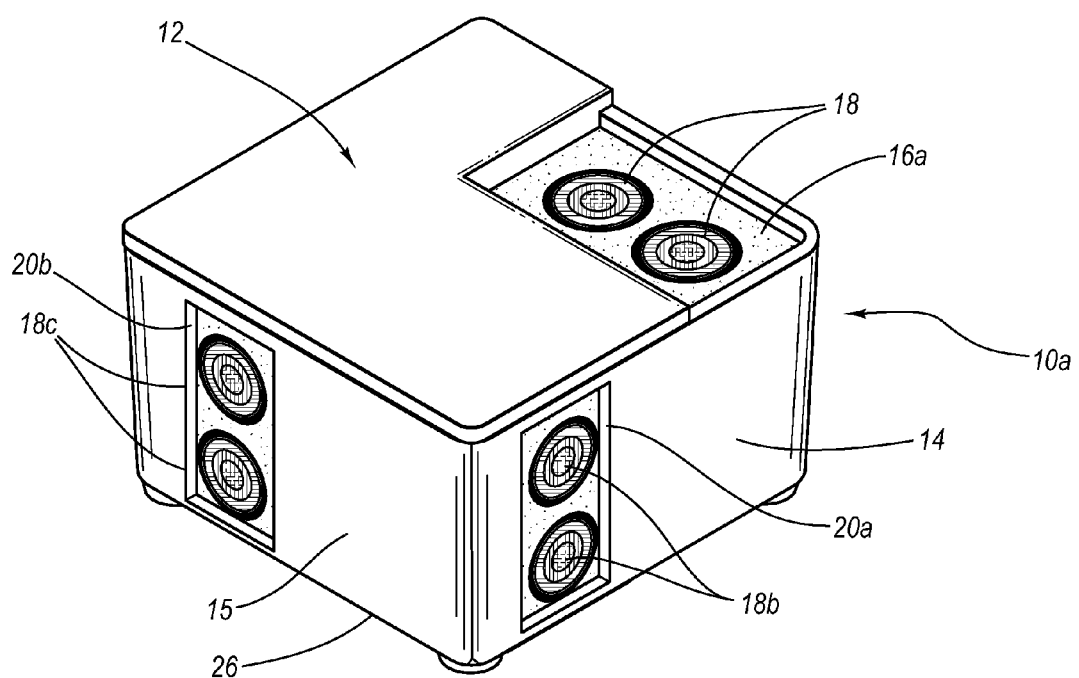

FIG. 6B is an illustrative view of a temporary instrument holder 10a, according to one embodiment of the present invention. In the illustrated embodiment, a instrument holder field 16a having two targets 18a is positioned in a top surface 12 of the temporary instrument holder 10a. A lateral surface instrument holder aperture 20a having two targets 18b is positioned in a second side surface 14 of temporary instrument holder 10a. A second lateral surface instrument holder aperture 20 having two targets 18c is positioned in a second side surface 15. In this manner, both primary and secondary surfaces on the temporary instrument holder are provided with substantially identical instrument holder fields that can be utilized as desired by the practitioner. An arrangement as presently illustrated, in which the configuration of the instrument holder fields are substantially the same, while being provided at different locations on the temporary instrument holder, can be desirable where a procedure requires the organization and/or reuse of many similar sharp implements. Alternatively, a plurality of sharp implements which simply require repeated use and safe disposition throughout the course of the procedure may be utilized. According to one embodiment of the present invention, all or substantially all of the surfaces of the temporary instrument holder are provided with a instrument holder field, such that in the event that the temporary instrument holder is tipped, a instrument holder field is readily available for the disposition of needles, trocars, or other sharp implements that need to be disposed of According to some embodiments of the present invention, subsequent to the completion of the procedure, the entire temporary instrument holder 10a can be discarded without needing to remove the needles that have been inserted therein. In this manner, the temporary instrument holder 10a provides not only a safety mechanism for use during the course of the procedure, but also a quick, safe, and effective mechanism for disposing of the sharps subsequent to the completion of the procedure. Because lateral surface instrument holder apertures 20a and 20b allow for the positioning of heavier needles, syringes, tools, or other implements, the temporary instrument holder 10a functions not only as a sharps receptacle for smaller needle tips or lighter syringes, but also as a depository for all potentially sharp implements that may need to be discarded subsequent to the completion of the procedure.

Figure 7:
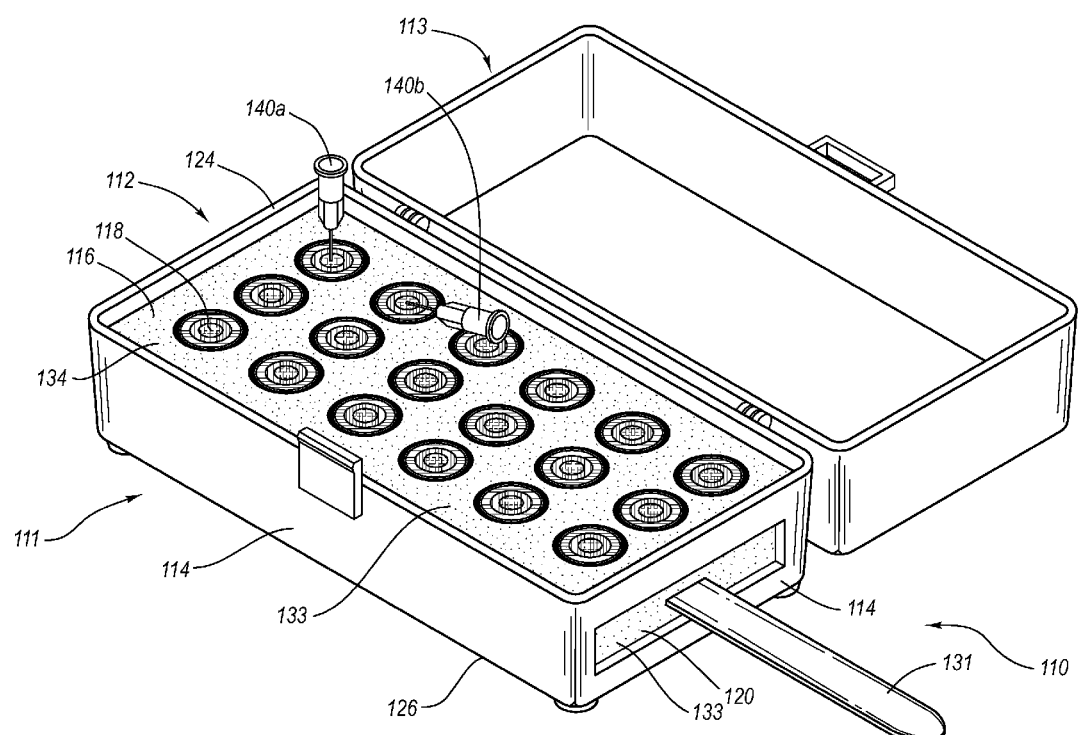
FIGS. 7-9 are perspective views of a temporary instrument holder having a lid and a plurality of instrument holder apertures, according to alternative embodiments of the invention.

FIG. 7 is a perspective view of a temporary instrument holder 110, according to one embodiment of the invention. In the illustrated embodiment, temporary instrument holder 110 has a lateral surface instrument holder aperture 120, which is utilized to allow for insertion of medical instruments, such as needles, trocars, scalpels or other devices or implements, into the side of temporary instrument holder 110. Insertion of such medical instruments into the side of temporary instrument holder 110 helps to reduce tipping of temporary instrument holder 110. In the illustrated embodiment, temporary instrument holder 110 includes a body 111, a lid 113, a top surface 112, side surfaces 114, a instrument holder field 116, lateral surface instrument holder aperture 120, a rim 124, a bottom 126, top instrument holder cushion layer 134, and lateral instrument holder cushion layer 133.

In one embodiment, body 111 of temporary instrument holder 110 provides a housing for instrument holder field 116. In the illustrated embodiment, body 111 comprises a generally box-like structure having side surfaces 114, rim 124 and bottom 126. Body 111 can be made of any suitable material, such as plastic or some other polymer. In the illustrated embodiment, lid 113 is linked to a side surface of body 111 via a hinge-type connection. Lid 113 is configured to enclose instrument holder field 116 when lid 113 is closed and positioned adjacent rim 124. The outer boundary of lid 113 may be sized to correspond and mate with rim 124. Furthermore, lid 113 and body 111 may include a latching device to substantially secure lid 113 to body 111.

In one embodiment, lid 113 is configured and sized such that its depth is sufficient to allow needle tips 140a-b to be positioned in instrument holder field 116 with lid 113 closed without having the needle tips 140a-b interfere with the complete closure of lid 113. In this manner, after a practitioner has disposed of various medical instruments, such as needle tips, the practitioner may close lid 113. Closing lid 113 encloses the needle tips in instrument holder field 116 to in turn reduce the risk of accidental puncture of the practitioner by the disposed medical devices. When lid 113 is closed, lid 113 may effectively serve as a boundary septum for lateral surface instrument holder aperture 120. In some other embodiments, lid 113 may include additional instrument holding fields.

Top surface 112 of temporary instrument holder 110 includes instrument holder field 116. Top surface 112 of temporary instrument holder 110 is configured such that it is facing upward allowing it to be easily viewed and accessed by a practitioner when lid 113 is open. A plurality of targets 118 are positioned in instrument holder field 116 to provide a visual identification of the potential placement areas for medical instruments, such as needles, trocars, scalpels or other sharp implements or tools that may be utilized during the course of a procedure. A practitioner can insert smaller and/or lighter needle apparatus, such as needle tips, emptied syringes, or an IV trocar into top surface 112.

Lateral surface instrument holder aperture 120 is positioned in side surface 114 of temporary instrument holder 110 in a manner that the practitioner can insert larger and/or heavier medical instruments such as a scalpel, a needle syringe combination, or some other sharp implement, into lateral surface needle aperture 120. Lateral surface instrument holder aperture 120 provides not only a supplementary instrument holder field for insertion of sharp devices, but is also positioned closer to the surgical surface, allowing for resting of the medical instrument on the surgical surface. Allowing for resting of the medical instrument on the surgical surface minimizes tipping of temporary instrument holder 110. Lateral surface instrument holder 120 is one example of a feature enabling insertion of a needle or other sharp device into a second side of the temporary instrument holder.

In the illustrated embodiment, lateral surface instrument holder aperture 120 is rectangular in shape. The shape and configuration of lateral surface instrument holder aperture 120 enables a variety of types, shapes and sizes of implementations to be inserted therein. For example, in the illustrated embodiment, a scalpel 131 has been inserted in lateral surface instrument holder aperture 120. The size and configuration of lateral surface instrument holder aperture 120 may be adjusted to accommodate for the size and configuration of various medical implements.

In the illustrated embodiment, a scalpel 131 is inserted in lateral surface instrument holder aperture 120. The positioning of scalpel 131 in lateral surface instrument holder aperture 120 facilitates the contact of scalpel 131 with a support surface. Being in contact with the support surface, scalpel 131 helps to reduce tipping of temporary instrument holder 110. In this manner, desired and intended positioning of temporary instrument holder 110 is maintained. This facilitates a practitioner to quickly identify instrument holder field 116 for the insertion of additional medical instruments such as needles, sharps or other tools or implements, while also being able to quickly identify the positioning of lateral surface instrument holder aperture 120 and scalpel 131 positioned therein.

Rim 124 is positioned to provide an outer boundary for instrument holder field 116. Rim 124 creates a slight recess between top surface 112 of temporary instrument holder 110 and the elevation of instrument holder field 116. In this manner, rim 124 prevents inadvertent slipping of sharp medical instruments from top surface 112 of instrument holder field 116 to the exterior of temporary instrument holder 110. In this manner, a practitioner can safely grasp temporary instrument holder 110 and insert a needle or other medical instrument into instrument holder field 116. In the event that the needle or some other medical instrument slips or does not entirely puncture instrument holder field 116, the tip of the medical instrument will typically be caught by rim 124. This catching generally prevents additional slipping and puncturing of the practitioner in an unexpected manner.

Bottom 126 is positioned on the side of temporary instrument holder 110 opposite top surface 112. Bottom 126 is configured to be positioned on a surgical or other medical work surface on which temporary instrument holder 110 is to be utilized. In one embodiment, bottom 126 includes a non-slip surface or adhesive surface which facilitates retention of temporary instrument holder 110 on the surgical surface and additionally prevents tipping of temporary instrument holder 110.

In the illustrated embodiment, lateral instrument holder cushion layer 133 extends a depth into temporary instrument holder 110. The size of the lateral instrument cushion layer 133 may correspond with and even extend beyond the location of lateral surface needle aperture 120. In this embodiment, lateral instrument holder cushion layer 133 substantially fills the volume of body 111 below rim 124. In this manner, needles or scalpels or other sharp implements which are inserted into instrument holder field 116 and/or lateral surface instrument holder aperture 120 are inserted into instrument holder cushion layer 133.

In the illustrated embodiment, the material from which lateral instrument holder cushion layer 133 is formed comprises a non-coring resilient foam material. The non-coring quality of instrument holder cushion layer 133 allows a needle to be inserted into instrument holder cushion layer 133 and withdrawn without leaving a noticeable hole. In this manner, a secondary implement can be reinserted into the same position without weakening or minimizing the ability of instrument holder cushion layer 133 to retain the secondary implement, subsequent to the earlier insertion.

As will be appreciated by those skilled in the art, a variety of types and configurations of temporary instrument holders can be utilized without departing from the scope and spirit of the present invention. In one embodiment, a variety of types and configurations of cushion materials may be utilized. For example, in one embodiment, a thermoplastic rubber layer can be utilized. In another embodiment, another resilient polymer-based material can be utilized. In another embodiment, small layers of foam can be positioned adjacent one another in a manner to retain a needle or other sharp implement.

Figure 8:
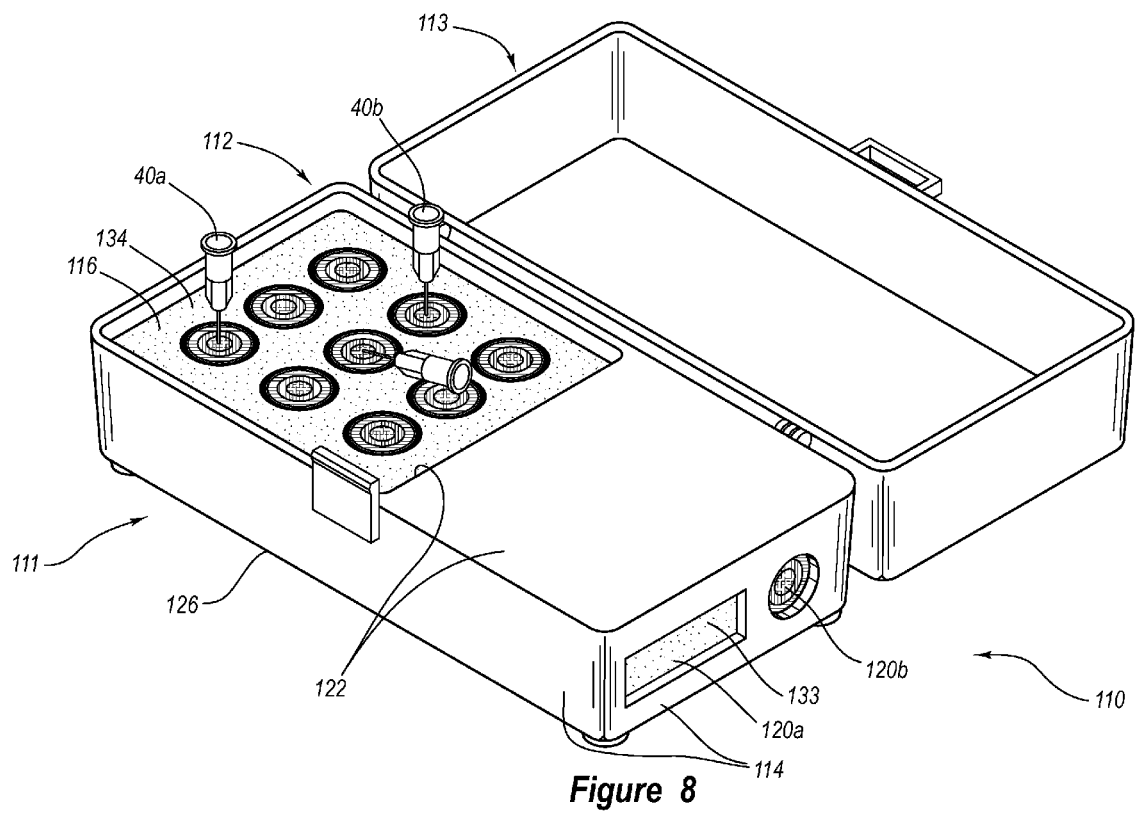

FIG. 8 illustrates an alternative embodiment of temporary instrument holder 110. In this embodiment, a first lateral surface instrument holder aperture 120a and a second lateral surface instrument holder aperture 120b are positioned in side surface 114 of the temporary instrument holder 110. In the illustrated embodiment, first lateral surface instrument holder aperture 120a is positioned to the side of second lateral surface instrument holder aperture 120b. First lateral surface instrument holder aperture 120a is larger and a different shape than second lateral surface instrument holder aperture 120b; first lateral surface instrument holder aperture 120a is rectangular and second lateral surface instrument holder aperture 120b is circular. This enables different types and sizes of medical implements to be placed in either the first or second lateral surface instrument holder apertures 120a-b, respectively. As a result, an implement, such as a scalpel, may be inserted into first lateral surface instrument holder aperture 120a and a needle combination may be placed in second lateral surface instrument holder aperture 120b. A plurality of lateral surface instrument holder apertures may be provided in the same side surface of temporary instrument holder 110, providing additional placement locations and potential sharps device organization by the practitioner during the course of the procedure.

Further illustrated in FIG. 8 is a boundary septum 122 separating lateral surface instrument holder apertures 120a-b from instrument holder field 116. In one embodiment, boundary septum 122 runs from top surface 112 of temporary instrument holder 110 to bottom 126 of temporary instrument holder 110, and extends from one side of body 111 to the opposing side of body 111. In this manner, boundary septum 122 may provide a complete and effective boundary to prevent the passage of sharps from instrument holder cushion layer 134 to lateral surface instrument holder apertures 120a-b.

In the illustrated embodiment, instrument holder field 116 comprises a top instrument holder cushion layer 134. In this embodiment, top instrument holder cushion layer 134 is rectangular shaped to correspond to a portion of body 111 defined by three side surfaces of body 111, bottom 126 and boundary septum 122. Lateral surface instrument holder apertures 120a-b comprise a side instrument holder cushion layer 138. In the illustrated embodiment, side instrument holder cushion layer 138 substantially fills the volume of body 111 defined by three side surfaces 114, bottom 126 and boundary septums 122.

As will be appreciated by those skilled in the art, a variety of types and configurations of temporary instrument holders may be utilized without departing from the scope and spirit of the present invention. For example, in one embodiment the boundary septum extends only a portion of the length from the top surface of the instrument holder cushion layer to the bottom of the instrument holder cushion layer.

Figure 9:
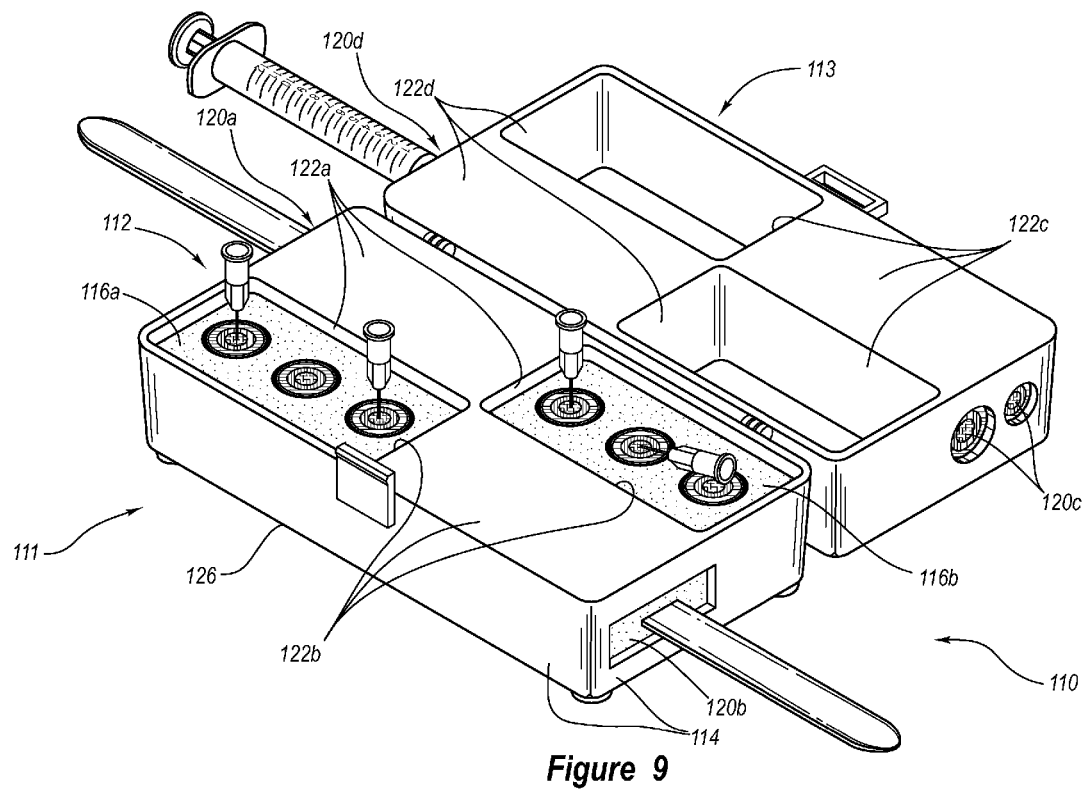

FIG. 9 is an illustrative view of a temporary instrument holder 110a, according to one embodiment of the invention. In the illustrated embodiment, body 111 of temporary instrument holder 110 comprises first and second instrument holder fields 116a-b positioned in top surface 112 of temporary instrument holder 110 and first and second lateral surface instrument holder apertures 120a-b positioned in opposing side surfaces 114 of temporary instrument holder 110. In this embodiment, each of first and second instrument holder fields 116a-b are positioned proximate opposing corners of body 111. Likewise, each of first and second lateral surface instrument holder apertures 120a-b may be positioned in opposing corners of body 111.

A first boundary septum 122a separates first lateral surface instrument holder aperture 120a from first instrument holder field 116a, second instrument holder field 116b and second lateral surface instrument holder aperture 120b. In one embodiment, first boundary septum 122a runs from top surface 112 of temporary instrument holder 110 to bottom 126 of temporary instrument holder 110. In this manner, first boundary septum 122a may provide a complete and effective boundary to prevent the passage of scalpels, needles, sharps, or other implements between first lateral surface instrument holder aperture 120a and first and second instrument holder fields 116a-b and second lateral surface instrument holder aperture 120b.

A second boundary septum 122b separates second lateral surface instrument holder aperture 120b from first instrument holder field 116a, second instrument holder field 116b and first lateral surface instrument holder aperture 120a. In one embodiment, second boundary septum 122b runs from top surface 112 of temporary instrument holder 110 to bottom 126 of temporary instrument holder 110. In this manner, second boundary septum 122b may provide a complete and effective boundary to prevent the passage of scalpels, needles, sharps, or other implements between second lateral surface instrument holder aperture 120b and first and second instrument holder fields 116a-b and first lateral surface instrument holder aperture 120a. In this embodiment, four separate cushion layers are provided—one for each of the first and second instrument holder fields 116a-b and one each for the first and second lateral surface instrument holder apertures 120a-b.

Further illustrated in FIG. 9 are a third lateral surface instrument holder aperture 120c and associated third boundary septum 122c, and a fourth lateral surface instrument holder aperture 120d (not shown) and associated fourth boundary septum 122d in lid 113. In the illustrated embodiment, third boundary septum 122c may provide a complete boundary to prevent the passage of scalpels, needles, sharps, or other implements from third lateral surface instrument holder aperture 120c. Likewise, fourth boundary septum 122d may provide a complete boundary to prevent the passage of scalpels, needles, sharps, or other implements from fourth lateral surface instrument holder aperture 120d. The positioning of third and fourth lateral surface instrument holder apertures 120c-d in lid 113 provides additional locations for a practitioner to place medical implements while not in use. Furthermore, positioning of third and fourth lateral surface instrument holder apertures 120c-d in lid 113 enables a practitioner to effectively utilize the space of temporary instrument holder 110.

An arrangement as presently illustrated may be desirable where a procedure requires the organization and/or reuse of many similar sharp implements. Alternatively, a plurality of sharp implements which simply require repeated use and safe disposition throughout the course of the procedure may be utilized. According to one embodiment of the present invention, all or substantially all of the surfaces of the temporary instrument holder are provided with a instrument holder field, such that in the event that the temporary instrument holder is tipped, a instrument holder field is readily available for the disposition of needles, trocars, or other sharp implements that need to be disposed.

According to some embodiments of the present invention, subsequent to the completion of the procedure, the entire temporary instrument holder 110 may be discarded as a unit including any used instruments inserted into temporary instrument holder 110. This allows the disposal of contaminated instruments without needing to remove the needles and/or instruments that have been inserted into the temporary instrument holder 110. In this manner, temporary instrument holder 110 provides not only a safety mechanism for use during the course of the procedure, but also a quick, safe, and effective mechanism for disposing of the sharps subsequent to the completion of the procedure. Because lateral surface instrument holder apertures allow for the positioning of heavier needles, syringes, tools, or other implements, temporary instrument holder 110 functions not only as a sharps receptacle for smaller needle tips or lighter syringes, but also as a depository for all potentially sharp implements that may need to be discarded subsequent to the completion of the procedure.

As will be appreciated by those of skill in the art, a variety of types and configurations of temporary instrument holders can be provided without departing from the scope and spirit of the present invention. For example, in one embodiment a different number and configuration of targets are provided in the instrument holder field. In another embodiment, the lateral surface instrument holder aperture is of a different size, shape and/or configuration. In another embodiment, the lid is sized and configured so as to enclose both instrument holder field and lateral surface instrument holder aperture.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A temporary instrument holder comprising:
    a instrument holder cushion layer having a surface positioned in an upward facing surface of the temporary instrument holder and being configured to receive a medical instrument therein, wherein the instrument holder cushion layer is configured to removably retain the medical instrument;
    a covering configured to enclose the instrument holder cushion layer;
    a lateral instrument holder aperture positioned in a side surface of the temporary instrument holder, the lateral instrument holder aperture facing in a different lateral direction than the upward facing surface of the temporary instrument holder cushion layer, the lateral instrument holder aperture being configured to allow the insertion of a medical instrument therethrough and being associated with a side instrument holder cushion layer, the lateral instrument holder aperture being positioned in a side surface of the temporary instrument holder cushion layer such that instruments introduced through the lateral instrument holder aperture are positioned in an insertion surface of the side instrument holder cushion layer;
    a boundary septum positioned between the instrument holder cushion layer and the side instrument holder cushion layer; and
    a top surface positioned adjacent the boundary septum and covering a top surface of the side needle holder cushion layer, wherein the combination of the boundary septum and the top surface provide an effective boundary to prevent a needle or other sharp device which is positioned in the side needle holder cushion layer to extend from the side instrument holder cushion layer to any secondary insertion surface in a manner that could result in the inadvertent puncture of the skin of the practitioner.

2. The temporary instrument holder of claim 1, further comprising:
    a second instrument holder aperture; and
    a septum configured to prevent passage of any portion of a medical instrument between the lateral instrument holder aperture and the second instrument holder aperture.

3. The temporary instrument holder of claim 1, further comprising one or more supplementary lateral instrument holder apertures.

4. The temporary instrument holder of claim 3, wherein at least one of the one or more supplementary lateral instrument holder apertures is located adjacent to the lateral instrument holder aperture.

5. The temporary instrument holder of claim 3, wherein at least one of the one or more supplementary lateral instrument holder apertures is positioned in a different side of the temporary instrument holder than the lateral instrument holder aperture.

6. The temporary instrument holder of claim 3, wherein at least one of the one or more supplementary lateral instrument holder apertures are positioned in the covering of the temporary instrument holder.

7. The temporary instrument holder of claim 3, wherein each of the one or more supplementary lateral instrument holder apertures is configured to allow access to the instrument holder cushion layer.

8. The temporary instrument holder of claim 3, further comprising
    one or more supplementary side instrument holder cushion layers, wherein each of the one or more supplementary lateral instrument holder apertures is associated with one of the one or more supplementary side instrument holder cushion layers.

9. The medical instrument of claim 8, further comprising one or more supplementary boundary septums positioned so as to separate the instrument holder cushion layer, the one or more supplementary side instrument holder cushion layers, and the side instrument holder cushion layer from each other.

10. A temporary instrument holder comprising:
a body, the body including an instrument holder aperture and a lateral instrument holder aperture;
an instrument holder cushion layer associated with the instrument holder aperture and configured to receive and hold a medical instrument inserted through the instrument holder aperture;
a lateral instrument holder cushion layer associated with the lateral instrument holder aperture, and configured to receive and hold a medical instrument inserted through the lateral instrument holder aperture;
a lid connected to the body, and configured to selectively cover the instrument holder aperture; and
a boundary septum positioned between the instrument holder cushion layer and the lateral instrument holder aperture,
a top surface covering the lateral instrument cushion layer, wherein the combination of the boundary septum and the top surface substantially prevent passage of any portion of a medical instrument between the lateral instrument holder aperture and the instrument holder aperture wherein the instrument holder cushion layer is positioned in a first side of the temporary instrument holder and the lateral instrument holder cushion layer is positioned in a second side of the temporary instrument holder, and wherein the instrument holder aperture is located in the first side and the lateral instrument holder aperture is located in the second side, and instrument holder aperture and the lateral instrument holder aperture are facing in different lateral directions; and
at least one supplementary lateral instrument holder aperture wherein the at least one supplementary lateral instrument holder aperture is located on a third side of the temporary instrument holder.

11. A temporary needle holder configured to receive needles, trocars, or other devices or implements therein to minimize the exposure of such sharps to a surgical environment in a manner that could result in inadvertent puncturing of the skin of a practitioner subsequent to completion of the use of the device or implement, the temporary needle holder comprising:
a first needle holder cushion layer having a first needle holder field comprising a first insertion surface positioned in an upper surface of the temporary needle holder, the first needle holder field and first needle holder cushion layer being configured to allow insertion of a needle or other sharp device therein and to retain the needle or other sharp device without assistance from the practitioner;
a side needle holder cushion layer having a second needle holder field comprising a second insertion surface positioned in a side surface of the temporary needle holder, the second needle holder field and side needle holder cushion layer being configured to allow insertion of a needle or other sharp device therein and withdrawal of the needle or other sharp device there from, wherein the side needle holder cushion layer is configured to retain the needle or other sharp device without assistance from the practitioner;
a boundary septum positioned between the first needle holder field and the second needle holder field; and
a top surface positioned adjacent the boundary septum, the top surface forming a covering for the side needle holder cushion layer, wherein the combination of the boundary septum and the top surface provide an effective boundary to prevent a needle or other sharp device which is positioned in the side needle holder cushion layer to extend from the side needle holder cushion layer to any secondary needle holder field in a manner that could result in the inadvertent puncture of the skin of the practitioner.

12. The temporary instrument holder of claim 11, further comprising a second side needle holder cushion layer configured to receive and retain at least one medical instrument therein.

13. The temporary instrument holder of claim 11, wherein the boundary septum is configured to substantially prevent the passage of a needle or other implement from the first needle holder cushion layer to the side needle holder cushion layer.

14. The temporary instrument holder of claim 13, wherein the boundary septum is positioned between the first needle holder cushion layer and the side needle holder cushion layer.

15. The temporary instrument holder of claim 5, wherein the boundary septum is positioned between the side needle holder cushion layer and the second side needle holder cushion layer.

16. The temporary instrument holder of claim 11, further comprising a lid configured to selectively enclose the first instrument holder portion.

17. The temporary instrument holder of claim 16, wherein the lid is unobstructed by a needle inserted and retained in the first instrument holder portion when the lid is in a closed configuration.

18. The temporary instrument holder of claim 11, further comprising one or more supplementary instrument holder portions.

* * * * *